United States Patent [19]

Drent

[11] Patent Number: 4,739,110

[45] Date of Patent: Apr. 19, 1988

[54] PROCESS FOR THE CARBONYLATION OF ALLENICALLY UNSATURATED COMPOUNDS

[75] Inventor: Eit Drent, Amsterdam, Netherlands

[73] Assignee: Shell Oil Company, Houston, Tex.

[21] Appl. No.: 814,347

[22] Filed: Dec. 27, 1985

[30] Foreign Application Priority Data

Jan. 25, 1985 [GB] United Kingdom ............... 8501919

[51] Int. Cl.$^4$ .................. C07C 51/14; C07C 67/38
[52] U.S. Cl. .................. 560/207; 560/104,114,130; 562/406,497,522; 260/546
[58] Field of Search ............... 560/207, 104, 114, 130, 560/546; 562/522, 497, 406; 260/546

[56] References Cited

U.S. PATENT DOCUMENTS

| | | | |
|---|---|---|---|
| 2,738,364 | 3/1956 | Reppe et al. | 562/522 |
| 3,501,518 | 3/1970 | Kutepow et al. | 260/468 |
| 3,641,137 | 2/1972 | Fenton | 260/546 |
| 3,709,927 | 1/1973 | Kunichika | 562/522 |
| 3,887,595 | 6/1975 | Nozaki | 560/207 |
| 3,904,672 | 9/1975 | Knifton | 560/207 |
| 3,952,034 | 4/1976 | Thompson | 560/207 |
| 4,055,721 | 10/1977 | Kawata et al. | 562/522 |
| 4,380,121 | 10/1984 | Klun et al. | 560/207 |

FOREIGN PATENT DOCUMENTS 0106379 4/1984 European Pat. Off. .
1110405 4/1968 United Kingdom .

*Primary Examiner*—Michael L. Shippen

[57] ABSTRACT

A process for the carbonylation of an allenically unsaturated compound with CO in the presence of water, an alcohol and/or a carboxylic acid, which process is carried out in the presence of a catalyst formed by combining:

(a) a compound of divalent palladium,
(b) at least 15 mol of an organic phosphine per gram atom of divalent palladium, and
(c) a protonic acid having a $pK_a$ greater than 1.5 and/or a carboxylic acid having a $pK_a$ not greater than 1.5, both measured at 18° C. in aqueous solution.

16 Claims, No Drawings

PROCESS FOR THE CARBONYLATION OF ALLENICALLY UNSATURATED COMPOUNDS

FIELD OF THE INVENTION

The invention relates to a process for the carbonylation of allenically unsaturated compounds with carbon monoxide in the presence of water, an alcohol and/or a carboxylic acid.

BACKGROUND OF THE INVENTION

It is known that allenes may be carbonylated in the presence of water or alcohols to yield carboxylic acids or esters, respectively. However, the known processes have various drawbacks which render them rather unattractive for use on a technical scale.

British Patent Specification No. 1,110,405 describes carbonylation of allene in the presence of a palladium halide and an organic phosphine. U.S. Pat. No. 3,501,518 describes carbonylation of polyolefinically unsaturated compounds in the presence of a palladium chalcogenide, an organic phosphine and an acid. The necessity of using extremely high partial pressures of carbon monoxide is a disadvantage of these known processes.

European Patent Application No. 106,379 describes carbonylation of olefinically unsaturated compounds having two double bonds in the presence of a palladium catalyst, at least 5 mol of a triarylphosphine per gram atom palladium and an acid having a $pK_a$ below 2, except hydrohalogenic and carboxylic acids. This known process has an advantage that high reaction rates are obtained at relatively low partial pressures of carbon monoxide.

It has now been found that allenically unsaturated compounds are rapidly carbonylated at relatively low pressure by using a catalytic system in which protonic acids having a $pK_a$ greater than 1.5 and/or carboxylic acids having a $pK_a$ not greater than 2.0 are combined with at least 15 mol of organic phosphine per gram atom of divalent palladium.

SUMMARY OF THE INVENTION

The invention, therefore, provides a process for the carbonylation of allenically unsaturated compounds with carbon monoxide in the presence of water, an alcohol and/or a carboxylic acid, which process is carried out in the presence of a catalytic system comprising:
(a) a compound of divalent palladium,
(b) an amount of at least 15 mol of an organic phosphine per gram atom of divalent palladium, and
(c) a protonic acid having a $pK_a$ greater than 1.5 and/or a carboxylic acid having a $pK_a$ not greater than 1.5, both measured at 18° C. in aqueous solution.

DESCRIPTION OF THE PREFERRED EMBODIMENTS

It has been found that the process according to the present invention exhibits a very high selectivity to carboxylic acids, esters or carboxylic anhydrides, starting from water, alcohols or carboxylic acids, respectively. The selectivity to a certain compound expressed in a percentage is defined as a/b × 100 in which "a" is the amount of allenically unsaturated compound that has been converted into that certain compound and "b" is the total amount of allenically unsaturated compound that has been converted.

Both homogeneous and heterogeneous palladium catalysts may be used in the process according to the invention. Homogeneous catalysts are preferred. Suitable homogeneous catalysts are the salts of palladium with, for example, nitric acid, sulfuric acid or alkanoic acids having not more than 12 carbon atoms per molecule. Salts of hydrohalogenic acids, in principle, may be used as well, but they have the drawback that the halogen ion may have a corrosive effect. A palladium compound used by preference is palladium acetate. Moreover, palladium complexes may be used, such as, for instance, palladium acetylacetonate, tetrakistriphenylphosphinepalladium, bis-tri-o-tolylphosphinepalladium acetate or bistriphenylphosphinepalladium sulphate. Palladium bonded to an ion exchanger such as, for instance, an ion exchanger comprising sulfonic acid groups, is an example of a suitable heterogeneous catalyst. Mixtures of two or more compounds of divalent palladium may be used.

The organic phosphine may be primary, secondary or tertiary, which is preferred. Suitable phosphines include those of the general formula I

in which $R^1$, $R^2$ and $R^3$ each independently represent an optionally substituted alkyl group, an optionally substituted cycloalkyl group or an optionally substituted aryl group or $R^2$ and $R^3$ together represent an optionally substituted alkylene or phosphacycloalkylene group. Preferably, a suitable alkyl group has up to 20 carbon atoms, a suitable cycloalkyl group up to 5 to 7 carbon atoms in the ring and a suitable aryl group up to 18 carbon atoms in the ring. A suitable aryl group may be, for example, an anthryl, naphthyl or a phenyl group, which is preferred. Phosphines of the general formula I in which $R^1$ and $R^2$ each represent an optionally substituted phenyl group are a preferred group of phosphines. Within this group, those phosphines in which $R^3$ also represents an optionally substituted phenyl group are particularly preferred. Very good results have been obtained with triphenylphosphine.

An optionally substituted alkylene group formed by $R^2$ and $R^3$ suitably has in the range of from 4 to 9 and particularly from 6 to 8 carbon atoms, and such a group may form a monocyclic or a bicyclic ring containing the phosphorous atom. An example of such a compound is

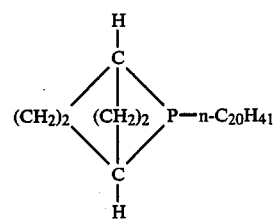

Another preferred group of organic phosphines are those of the general formula I in which $R^3$ represents a chain of carbon atoms ending with the group $-PR^4R^5$, in which R[4] represents an optionally substituted phenyl group and R[5] an optionally substituted alkyl, optionally substituted cycloalkyl or optionally substituted phenyl group. Within this group, R[1] and R[2] preferably represent an optionally substituted phenyl group. Preferred compounds are 1,5-di(diphenylphosphino)pentane and 1,6-di(diphenylphosphino)hexane. Preferably, R[4] and R[5] are equal to R[1] and R[2], respectively. The chain of carbon atoms suitably comprises 2 to 6 carbon atoms and preferably comprises 2 to 6 methylene groups.

An aryl group present in the organic phosphine of the catalytic system may carry an electron-donating substituent, such as an alkyl group, a p-alkoxy group (para with respect to the carbon-phosphorous bond) and a dialkylamino group. The alkyl groups and p-alkoxy groups preferably have no more than 5 carbon atoms; examples of such groups are methyl, ethyl, propyl, isopropyl, butyl, sec-butyl and tert-butyl groups. An example of a suitable phosphine is tri(p-methoxyphenyl)phosphine.

The phosphines used in the process according to the invention may carry electron-withdrawing substituents on any aryl group. Examples of electron-withdrawing substituents are halogen atoms and m-alkoxy and halomethyl groups, "halo" referring to iodo, bromo, chloro and fluoro; the halomethyl groups include mono-, di- and trihalomethyl groups. Very good results have been obtained with tri(p-chlorophenyl)phosphine in combination with orthophosphoric acid.

Other examples of suitable phosphines are phenyldiethylphosphine, ethyldiphenylphosphine, phenyldipropylphosphine, propyldiphenylphosphine, tri-o-tolylphosphine, phenyl-di-butylphosphine, diphenylmethylphosphine, tricyclohexylphosphine, tri-n-butylphosphine and tri-n-octylphosphine. Further examples of suitable phosphines are 1,2-di(diphenylphosphino)ethane, 1,2-di(diphenylphosphino)ethene, 1,2-di(diphenylphosphino)ethylene, 1,2-di(diphenylphosphino)benzene, 1,2-diphenylphosphino-tetrafluoro-1,2-cyclobutene, 1,2-diphenylphosphino-hexafluoro-1,2-cyclopentene, 1,2-diphenylphosphino-octafluoro-1,2-cyclohexene, 1,4-diphenyl-1,4-diphosphacyclohexane, bis(o-diphenylphosphinophenyl)phenylphosphine and tris(o-diphenylphosphinophenyl)phosphine.

Mixtures of two or more organic phosphines may be used.

The protonic acid having a $pK_a$ greater than 1.5 which is used in the process according to the present invention may be inorganic or organic. Examples of inorganic acids are arsenic acid and orthophosphoric acid. Examples or organic acids are formic acid, acetic acid, acetoacetic acid, benzoic acid, n-butyric acid, methacrylic acid, monochloroacetic acid, 2,4,6-trihydroxybenzoic acid and terephthalic acid. Very good results have been obtained with benzenephosphonic acid. Examples of carboxylic acids having a $pK_a$ not greater than 1.5 are dichloroacetic acid, trichloroacetic acid and oxalic acid. Trifluoroacetic acid is a particularly preferred acid.

Mixtures of two or more protonic acids having a $pK_a$ greater than 1.5 and/or of two or more carboxylic acids having a $pK_a$ not greater than 1.5 may be used.

Modifying the process according to the present invention by using less than 15 mol organic phosphine per gram atom palladium results in a very low reaction rate and a decreased selectivity to carboxylic acids, esters or carboxylic anhydrides. Preferably, in the range of from 20 to 500 mol of organic phosphine are used per gram atom of palladium; use of more than 500 mol is, however, not excluded.

The quantity of the compound of divalent palladium is not critical. Preference is given to the use of quantities in the range between $10^{-5}$ and $10^{-1}$ gram atom palladium per mol of allenically unsaturated compound.

The number of equivalents of the organic phosphine which is used per equivalent of protonic acid is not critical and may vary between wide limits. Suitably, in the range of from 0.2 to 50 equivalents of the organic phosphine are used per equivalent of the protonic acid.

A separate solvent is not essential in the prcoess according to the invention, and often a large excess of one of the reactants, usually the alcohol, may form a convenient liquid phase. However, it may in some cases be desirable to use a separated solvent and any inert solvent may be used. A suitable solvent may for example be selected from sulphoxides and sulphones, for example dimethyl sulphoxide, diisopropyl sulphone or tetrahydrothiophene 1,1-dioxide (also referred to as "sulfolane") and ethers. Very good results have been obtained with ethers, in particular with anisole, 2,5,8-trioxanonane (also referred to as "diglyme") and diphenyl ether. Another example of a suitable ether is diisopropyl ether.

The process according to the invention permits the use of very mild reaction conditions. Temperatures in the range of from 50° C. to 200° C., especially 100° C. to 150° C., are generally suitable. The pressure may vary over a wide range. Generally, a pressure in the range of from 1 to 100 bar is suitable, with pressures of from 5 to 50 bar being preferred. Pressures higher than 100 bar may be used, but are usually economically unattractive.

The molar ratio of alcohol (or water or carboxylic acid) to allenically unsaturated bonds is not critical, may vary between wide limits and is generally in the range of from 0.1:1 to 10:1.

The process according to the invention may be carried out using a wide variety of allenically unsaturated compounds and includes such compounds carrying one or more substituents which are inert under the reaction conditions, such as halogen atoms and cyano, ester, alkoxy and aryl groups. In addition, the allenically unsaturated compound may contain one or more substituents which are not inert under the reaction conditions such as, for example, hydroxy groups. The fate of such groups will depend on the precise reaction conditions. One or more allenically unsaturated bonds may be present in any position in the carbon chain. Very good results have been obtained with unsubstituted alkadienes, particularly with those having up to 20 carbon atoms per molecule, more particularly with allene. Other examples of suitable allenes are 1,2-butadiene, 1,2-pentadiene, 3,4-octadiene and 3-methyl-1,2-butadiene. The allenically unsaturated compound may be used pure, diluted with an inert compound or diluted with a compound which is not inert under the reaction conditions. An example of the latter case is a mixture of an allenically and an acetylenically unsaturated compound, such as allene mixed with propyne, as becomes available by cracking of hydrocarbons in the presence of steam for the production of ethylene. Acetylenically and ethylenically unsaturated compounds are both carboxylated when the organic phosphine is a phosphine of the general formula I in which any aryl group is unsubstituted or carries an electro-donating substituent and the protonic acid is a non-carboxylic protonic acid having a $pK_a$ greater than 1.5 or a carboxylic acid. Carbonylation of acetylenically unsaturated compounds is described in British Patent Application No. 8432376.

A wide range of alcohols may be used as reactant in the process of the invention. For example, the alcohol may be aliphatic, cycloaliphatic or aromatic, and may carry one or more inert substituents, for example halogen atoms and cyano, ester, alkoxy and aryl groups. The alcohol suitably contains up to 20 carbon atoms per molecule. One or more hydroxy groups may be present, in which case different products can be obtained as desired, depending upon the molar ratio of reactants used. For example, a trihydric alcohol can be reacted with a small quantity of allenically unsaturated compound to produce a mono-ester, or with a large quantity of allenically unsaturated compound to produce a tri-ester.

Thus, the choice of alcohol depends solely on the desired product. The use of water produces alpha-beta unsaturated carboxylic acids as the initial product. The use of alcohols produces alpha-beta-unsaturated esters, and these can of course be poly-esters as described above. Alkanols such as methanol, ethanol, propanol, isobutanol, tert.-butanol, stearyl alcohol, benzyl alcohol, cyclohexanol, allyl alcohol, chlorocapryl alcohol, ethylene glycol, 1,2-dihyrooxypropane, 1,4-dihydroxybutane, glycerol, 1,6-hexanediol, phenol or 2,2-dihydroxymethyl-1-butanol, and alcohols containing ether linkages such as, for example, triethylene glycol, may all be used.

A wide range of carboxylic acids may be used as a reactant in the process according to the invention. This carboxylic acid may be the same as or different from the protonic acid having a $pK_a$ greater than 1.5 and present in the catalytic system. The carboxylic acid may be aliphatic, cycloaliphatic or aromatic, and may carry one or more inert substituents such as, for example, halogen atoms and cyano, ester, alkoxy and aryl groups. The carboxylic acid may contain one or more ethylenically and/or acetylenically unsaturated carbon-carbon bonds and suitably contains up to 20 carbon atoms per molecule. One or more carboxyl groups may be present, in which case different products can be obtained as desired, depending upon the molar ratio of reactants used. For example, a dicarboxylic acid can be reacted with a small quantity of allenically unsaturated compound to produce an anhydride containing a carboxyl group, or with a large quantity of allenically unsaturated compound to produce an anhydride free to carboxyl groups. Examples of carboxylic acids are those having up to 20 carbon atoms per molecule, such as formic acid, acetic acid, propionic acid, n-butyric acid, isobutyric acid, pivalic acid, valeric acid, hexanoic acid, octanoic acid, nonanoic acid, decanoic acid, dodecanoic acid, tetradecanoic acid, hexadecanoic acid, octadecanoic acid, benzoic acid, phthalic acid (o-, m- and p-) and toluic acid (o-, m- and p-).

In the process according to the invention, the carbon monoxide may be used pure or diluted with an inert gas, such as nitrogen, noble gases or carbon dioxide. Generally, the presence of more than 10%v of hydrogen is undesirable, since under the reaction conditions it may cause hydrogenation of the allenically unsaturated compound. Generally preference is given to the use of carbon monoxide or a carbon monoxide-containing gas which contains less than 5% by volume of hydrogen.

The following examples are intended for illustration and are not to be construed as limiting the invention.

EXAMPLES 1–5 AND COMPARATIVE EXPERIMENTS A–D

A 250 ml magnetically stirred Hastelloy C autoclave ("Hastelloy" is a trade mark) was charged with 10 ml methanol, 40 ml of a solvent and with palladium acetate, a phosphine and a protonic acid (if any). The Table hereinafter states which solvent, phosphine and protonic acid was used and the quantities of each of the three catalyst components. The autoclave was flushed with carbon monoxide, pressurized with allene until a partial allene pressure of 2 bar was reached and with carbon monoxide until a partial pressure of 20 bar was reached, sealed and heated to a temperature of 115° C. After the reaction time stated in the Table the contents of the autoclave were analysed by means of gas-liquid chromatography. The reaction rates and selectivities to methyl methacrylate are presented in the Table.

Example 1 shows that the reaction rate and the selectivity to methyl methacrylate are both very high when using benzene-phosphonic acid ($pK_a=1.8$) and 50 mol phosphine per gram atom palladium. Comparison of Examples 1 and 2 shows that decreasing the ratio mol phosphine to gram atom palladium to 15 results in a considerable decrease of the reaction rate and said selectivity.

Example 3 shows that the presence of trifluoroacetic acid gives very high reaction rates and selectivities to methyl methacrylate.

Example 4 shows that good results are obtained when using methacrylic acid ($pK_a=4.5$) and 25 mol phosphine per gram atom palladium.

Example 5 shows that reaction rate and selectivity to methyl methacrylate are both very high when using a triphenylphosphine in which each of the three phenyl groups carries an electron-withdrawing substituent in combination with a protonic acid having a $pK_a$ greater than 1.5.

Comparative Experiment A shows that using a ratio mol phosphine to gram atom palladium of 6 results in a very low reaction rate.

Comparative Experiments B and C show that reaction rate is very low when using a strong non-carboxylic protonic acid. Comparative Experiment C also shows that the combination of a phosphine having an electron-withdrawing substituent on the phenyl groups and a strong non-carboxylic protonic acid results in a very low reaction rate.

Comparative Experiment D shows that in the absence of a protonic acid the reaction rate is very low.

EXAMPLE 6

The experiment of Example 1 was repeated using 10 ml methacrylic acid instead of 10 ml methanol and 40 ml diphenyl ether instead of 40 ml anisole. The reaction rate was 1400 mol allene per gram atom palladium per hour and the selectivity to methacrylic anhydride 95%, measured after 0.5 h.

EXAMPLE 7

The experiment of Example 6 was repeated in the absence of benzenephosphonic acid. The reaction rate was 1100 mol allene per gram atom palladium per hour and the selectivity to methacrylic anhydride 92%, measured after 0.5 h.

TABLE

| Example No. | Comparative Experiment | Palladium Acetate mmol | Phosphine | Amount mmol | Protonic Acid | Amount mmol | Solvent | Reaction Time h | Reaction rate, mol allene per gram atom Pd per hour | Selectivity, %, to methyl methacrylate |
|---|---|---|---|---|---|---|---|---|---|---|
| 1 | | 0.2 | triphenylphosphine | 10 | benzenephosphonic acid | 10 | anisole | 1 | 1000 | 92 |
| 2 | | 0.2 | triphenylphosphine | 3 | benzene phosphonic acid | 3 | anisole | 5 | 80 | 80 |
| | A | 0.2 | triphenylphosphine | 1.2 | benzene phosphonic acid | 10 | anisole | 5 | less than 10 | 60 |
| 3 | | 0.2 | triphenylphosphine | 10 | trifluoroacetic acid | 10 | diphenyl ether | 0.5 | more than 1400 | 90 |
| | B | 0.5 | triphenylphosphine | 5 | hydrogen | 3 | anisole | 5 | less than 1 | — |
| 4 | | 0.2 | 1,6-di(diphenylphosphino)hexane | 5 | methacrylic acid | 10 | diphenyl ether | 5 | 200 | 90 |
| | C | 0.5 | tri(m-trifluoromethylphenyl) phosphine | 10 | p-toluenesulphonic acid | 10 | anisole | 5 | less than 10 | 80 |
| 5 | | 0.2 | tri(p-chlorophenyl)phosphine | 10 | orthophosphoric acid | 10 | diphenyl ether | 5 | 200 | 90 |
| | D | 0.2 | triphenylphosphine | 10 | none | | diphenyl ether | 5 | below 10 | — |

EXAMPLE 8

The experiment of Example 1 was repeated using 5 ml water instead of 10 ml methanol and 40 ml diglyme instead of 40 ml anisole. The reaction rate was more than 1000 mol allene per gram atom palladium per hour and the selectivity to methacrylic acid 85%, measured after 0.5 h.

EXAMPLE 9

The experiment of Example 1 was repeated using 10 mmol trifluoroacetic acid instead of 10 mmol benzenephosphonic acid, 40 ml diphenyl ether instead of 40 ml anisole and using 10 ml methacrylic acid. The reaction rate was more than 1400 mol allene per gram atom palladium per hour and the selectivity to methacrylic anhydride 90%, measured after 0.5 h.

EXAMPLE 10

The experiment of Example 1 was repeated using a partial allene pressure of 1.5 bar and a partial propyne pressure of 1.5 bar and 40 ml diphenyl ether instead of 40 ml anisole. The overall reaction rate was 320 mol (allene+propyne) per gram atom palladium per hour and the selectivity to methyl methacrylate was 91%, measured after 2 h.

I claim as my invention:

1. A process for the carbonylation of allenically unsaturated compounds which comprises contacting at a temperature in the range of from 50° C. to 200° C. allenically unsaturated compounds with carbon monoxide in the presence of a compound selected from the group consisting of water, an alcohol, a carboxylic acid and mixtures thereof to form the corresponding ethylenically unsaturated acid, ester or anhydride in the presence of a catalytic system comprising:
(a) a compound of divalent palladium,
(b) an amount of at least 15 mol of an organic phosphine per gram atom of divalent palladium, and
(c) a protonic acid having a $pK_a$ greater than 1.5 and/or a carboxylic acid having a $pK_a$ not greater than 1.5, both measured at 18° C. in aqueous solution.

2. The process of claim 1 wherein the organic phosphine has the general formula I

in which $R^1$, $R^2$ and $R^3$ each independently represent an alkyl group, a cycloalkyl group or an aryl group, or $R^2$ and $R^3$ together represent an alkylene or phosphacycloalkylene group.

3. The process of claim 2 wherein $R^1$, $R^2$ and $R^3$ each represent a phenyl group.

4. The process of claim 3 wherein the organic phosphine is triphenylphosphine.

5. The process of claim 2 wherein $R^1$ and $R^2$ each represent a phenyl group and $R^3$ represents a chain of carbon atoms ending with the group —$PR^4R^5$, in which $R^4$ represents a phenyl group and $R^5$ an alkyl, cycloalkyl or phenyl group.

6. The process of claim 5 wherein the chain of carbon atoms comprises 2 to 6 methylene groups.

7. The process of claim 6 wherein the phosphine is 1,6-di(diphenylphosphino)hexane.

8. The process of claim 1 wherein the protonic acid is benzenephosphonic acid.

9. The process of claim 1 wherein the carboxylic acid having a $pK_a$ not greater than 1.5 is trifluoroacetic acid.

10. The process of claim 1 wherein the compound of divalent palladium is palladium acetate.

11. The process of claim 1 wherein the range of from 20 to 500 mol of organic phosphine are used per gram atom of palladium.

12. The process of claim 1 wherein in the range of from 0.2 to 50 equivalents of the organic phosphine are used per equivalent of the protonic acid.

13. The process of claim 1 wherein an ether is used as a solvent.

14. The process of claim 1 wherein it is carried out at a total pressure in the range of from 1 to 100 bar.

15. The process of claim 1 wherein the allenically unsaturated compound is an alkadiene.

16. The process of claim 2 wherein the allenically unsaturated compound is mixed with an acetylenically unsaturated compound, the organic phosphine is a phosphine of the general formula I in which any aryl group is unsubstituted or carries an electron-donating substituent and the protonic acid is a non-carboxylic protonic acid having a $pK_a$ greater than 1.5 or a carboxylic acid.

* * * * *